(12) United States Patent
Tanaka et al.

(10) Patent No.: US 7,977,490 B2
(45) Date of Patent: Jul. 12, 2011

(54) PROCESS FOR PRODUCING THIAZOLE COMPOUND

(75) Inventors: Kazuyuki Tanaka, Oita (JP); Naoyuki Takano, Ibaraki (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 727 days.

(21) Appl. No.: 11/918,004

(22) PCT Filed: Apr. 5, 2006

(86) PCT No.: PCT/JP2006/307682
§ 371 (c)(1),
(2), (4) Date: Nov. 19, 2008

(87) PCT Pub. No.: WO2006/109811
PCT Pub. Date: Oct. 19, 2006

(65) Prior Publication Data
US 2011/0054185 A1 Mar. 3, 2011

(30) Foreign Application Priority Data
Apr. 7, 2005 (JP) .................. 2005-110702

(51) Int. Cl.
*C07D 277/28* (2006.01)
(52) U.S. Cl. ....................................... 548/202
(58) Field of Classification Search .................. 548/202
See application file for complete search history.

(56) References Cited

U.S. PATENT DOCUMENTS

| 4,125,719 A | 11/1978 | Grier et al. |
| 5,849,768 A | 12/1998 | Minamida et al. |
| 6,326,497 B1 | 12/2001 | Hamada |
| 6,403,803 B1 | 6/2002 | Rauchschwalbe |

FOREIGN PATENT DOCUMENTS

| EP | 0 446 913 | 9/1991 |
| EP | 0 794 180 | 9/1997 |
| JP | 05-208977 | 8/1993 |
| JP | 7-14916 | 2/1995 |
| JP | 2001-357877 | 12/2001 |
| SU | 798102 | 1/1981 |
| WO | 2005/123074 | 12/2005 |

OTHER PUBLICATIONS

Patent Abstracts of Japan, vol. 2000, No. 8, JP 2000-143648 (Nov. 1993).
Patent Abstracts of Japan, vol. 018, No. 075, JP 05-286936 (Feb. 1994).
Patent Abstracts of Japan, vol. 016, No. 180, JP 04-021674 (Jan. 1992).
Howard D. Hartough et al., "*Aminomethylation of Thiophene. II. The Intermediate N-(2-Thenyl)-formaldimines and their Reactions*", Journal of the American Chemical Society, vol. 70, pp. 4013-4017, (Dec. 1948).

Jerry March, "*Advanced Organic Chemistry*", John Wiley and Sons, New York, Section D, 6-13 (The Addition of Ammonia to Aldehydes and Ketones), p. 896, (1992).

*Primary Examiner* — Laura L. Stockton
(74) *Attorney, Agent, or Firm* — Wenderoth, Lind & Ponack, L.L.P.

(57) ABSTRACT

A process for producing a thiazole compound of the formula (3):

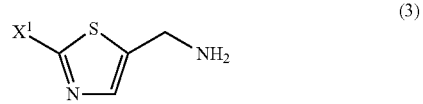

wherein $X^1$ is a hydrogen atom or a halogen atom, which comprises reacting a compound of the formula (1):

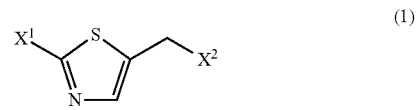

wherein $X^1$ is as defined above, and $X^2$ represents a halogen atom, with ammonia and formaldehyde to obtain a hexahydrotriazine compound of the formula (2):

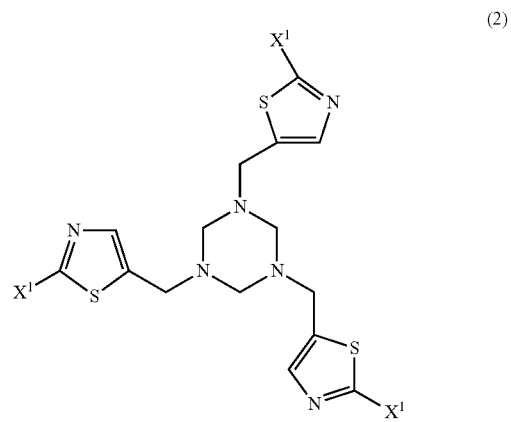

wherein $X^1$ is as defined above, and reacting the resulting hexahydrotriazine compound with hydroxylamine under acidic conditions. According to this process, the thiazole compound of the formula (3) can be industrially advantageously produced using inexpensive ammonia with suppressing the formation of a byproduct of the formula (4):

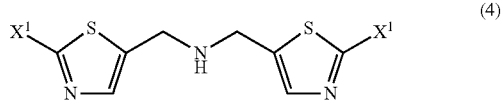

wherein $X^1$ is as defined above.

8 Claims, No Drawings

PROCESS FOR PRODUCING THIAZOLE COMPOUND

TECHNICAL FIELD

The present invention relates to a process for producing a thiazole compound.

BACKGROUND ART

A thiazole compound represented by the formula (3):

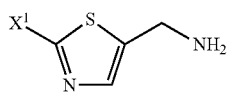

(3)

wherein $X^1$ represents a hydrogen atom or a halogen atom, a representative of which is 2-chloro-5-(aminomethyl)thiazole, is a compound useful as an intermediate for medicine and agrochemicals (see, for example, JP 7-14916 B). For producing it, several processes have been known. For example, there are (a) a process in which a compound represented by the formula (1):

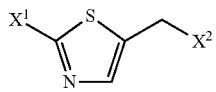

(1)

wherein $X^1$ is as defined above, and $X^2$ represents a halogen atom, is reacted with hexamethylenetetramine, followed by hydrolysis (see, for example JP 4-234864 A and JP 4-21674 A), (b) a process in which a compound represented by the above formula (1) is reacted with potassium phthalimide, followed by hydrazine degradation (see, for example JP 4-234864 A), (c) a process in which a compound represented by the above formula (1) is reacted with formamide, followed by hydrolysis (see, for example, JP 5-286936 A), and (d) process in which a compound represented by the above formula (1) is reacted with ammonia (see, for example, JP 4-234864 A and JP 2000-143648 A).

In all of the aforementioned processes (a) to (c), yields of the objective thiazole compound represented by the formula (3) are low, and those processes are unsatisfied from the industrial viewpoint. Although the process (d) is advantageous over the processes (a) to (c) in that more inexpensive ammonia is used, further improvement has been demanded because a considerable amount of a compound represented by the formula (4):

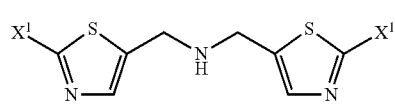

(4)

wherein $X^1$ is as defined above, is formed as a byproduct even when ammonia is used in the amount of 20 moles or more per mole of the compound represented by the above formula (1), and a yield of the objective thiazole compound represented by the formula (3) therefore is low.

DISCLOSURE OF THE INVENTION

Under the above circumstances, the present inventors have studied intensively to develop an industrially advantageous process for producing a thiazole compound represented by the formula (3) using inexpensive ammonia with suppressing the formation of a compound represented by the formula (4) as a byproduct. As a result, the present inventors have found that the objective thiazole compound represented by the formula (3) can be produced with suppressing the formation of the compound represented by the formula (4) as a byproduct by reacting a compound represented by the formula (1), ammonia, and formaldehyde which is also inexpensive and is easily available to obtain a hexahydrotriazine compound represented by the formula (2):

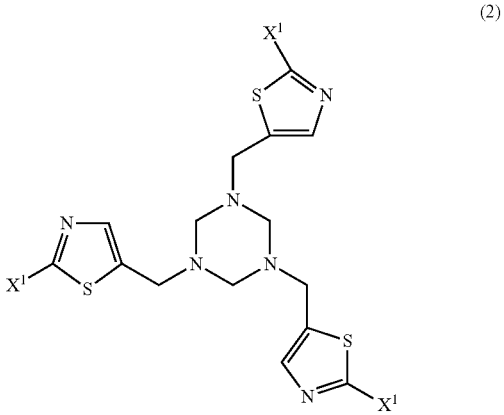

(2)

wherein $X^1$ is as defined above, followed by reacting the resulting compound represented by the formula (2) with hydroxylamine under acidic conditions. Thus, the present invention has been completed.

That is, the present invention provides a process for producing a thiazole compound represented by the formula (3):

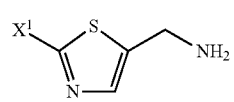

(3)

wherein $X^1$ represents a hydrogen atom or a halogen atom, which comprises the steps of reacting a compound represented by the formula (1):

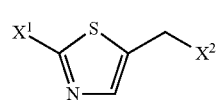

(1)

wherein $X^1$ is as defined above, and $X^2$ represents a halogen atom, with ammonia and formaldehyde to obtain a hexahydrotriazine compound represented by the formula (2):

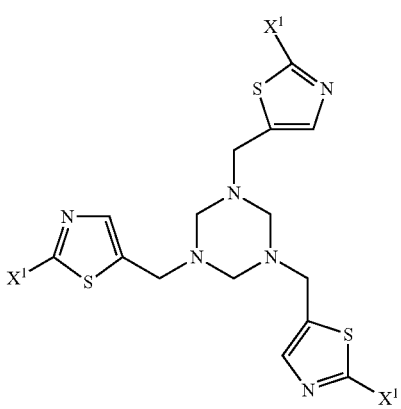

wherein $X^1$ is as defined above, and, then, reacting the resulting hexahydrotriazine compound represented by the formula (2) with hydroxylamine under acidic conditions, and the like.

BEST MODE FOR PERFORMING THE INVENTION

First, the step for reacting a compound represented by the formula (1):

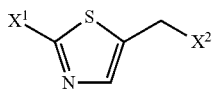

wherein $X^1$ represents a hydrogen atom or a halogen atom, and $X^2$ represents a halogen atom (hereinafter, abbreviated as the compound (1)), with ammonia and formaldehyde to obtain a hexahydrotriazine compound represented by the formula (2):

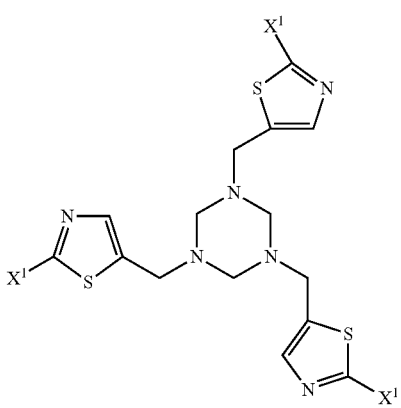

wherein $X^1$ is as defined above (hereinafter, abbreviated as the hexahydrotriazine compound (2)) will be explained.

In the formula of the compound (1), $X^1$ represents a hydrogen atom or a halogen atom, and $X^2$ represents a halogen atom. Examples of the halogen atom include a chlorine atom, a bromine atom, an iodine atom, etc.

Examples of the compound (1) include 5-(chloromethyl)thiazole, 2-chloro-5-(chloromethyl)thiazole, 2-chloro-5-(bromomethyl)thiazole, 2-bromo-5-(bromomethyl)thiazole, 2-chloro-5-(iodomethyl)thiazole, 2-bromo-5-(iodomethyl)thiazole, 2-iodo-5-(iodomethyl)thiazole, etc.

The compound (1) can be produced according to a known process as described, for example, in JP 4-234864 A.

The compound (1) may be in the form of a free compound or an acid addition salt. Examples of the acid for the acid addition salt include inorganic acids such as hydrogen chloride, hydrogen bromide, sulfuric acid, perchloric acid, etc., and organic acids such as acetic acid, methanesulfonic acid, trifluoromethanesulfonic acid, p-toluenesulfonic acid, etc.

As ammonia, an ammonia gas or liquid ammonia may be used. Alternatively, aqueous ammonia may be used. Further, a solution of ammonia dissolved in an organic solvent which can dissolve ammonia, such as methanol may be used. From a viewpoint of easy handling and a yield, preferably, a solution of ammonia in an organic solvent is used.

The amount of ammonia that may be used is usually 1 to 30 moles, preferably 2 to 15 moles, more preferably 2 to 10 moles per mole of the compound (1). When the acid addition salt is used as the compound (1), the amount of ammonia that may be used can be determined by taking into account the acid in the acid addition salt.

As formaldehyde, a formaldehyde gas may be used. However, from a viewpoint of handling, it is preferable to use paraformaldehyde or formalin, more preferably, paraformaldehyde. The amount of formaldehyde that may be used is usually 1 to 10 moles, preferably 1 to 8 moles, more preferably 1 to 5 moles per mole of the compound (1). In addition, preferably, the amount of ammonia that may be used relative to the compound (1) is greater than that of formaldehyde.

The reaction temperature is usually in the range of 15 to 100° C., preferably 20 to 90° C., and the reaction is performed usually under atmospheric pressure conditions or under pressurized conditions of 0.5 MPa (gauge pressure) or lower.

The reaction may be performed without a solvent, but is preferably performed in a solvent which is inert to the reaction. Examples of the solvent include alcohol solvents such as methanol, ethanol, n-propanol, isopropanol, etc., aromatic hydrocarbon solvents such as toluene, xylene, etc., halogenated hydrocarbon solvents such as chlorobenzene, dichlorobenzene, etc., aliphatic hydrocarbon solvents such as hexane, heptane, cyclohexane, etc., ether solvents such as diethyl ether, tetrahydrofuran, dioxane, etc., aprotic polar solvents such as acetonitrile, propionitrile, dimethylsulfoxide, N,N-dimethylacetamide, etc., water, and the like. These solvents can be used alone or in combination thereof. An alcohol solvent or water is preferable, and an alcohol solvent is more preferable. The amount of the solvent to be used is usually 1 to 10 parts by weight per 1 part by weight of the compound (1).

The reaction is performed by mixing and bringing into contact with the compound (1), ammonia and formaldehyde, and the mixing order of them is not specifically limited. For example, the compound (1), ammonia and formaldehyde may be mixed, and reacted at a predetermined temperature, or the compound (1) and formaldehyde are mixed in advance, and ammonia may be added thereto to react them. Alternatively, ammonia and formaldehyde are mixed in advance, and the compound (1) may be added thereto to react them. Alternatively, the compound (1) and ammonia may be simultaneously added to formaldehyde to react them, or the compound (1) and formaldehyde may be simultaneously added to ammonia to react them.

If necessary, the reaction may be performed in the presence of a quaternary ammonium salt such as triethylbenzylammonium chloride, tri-n-octylmethylammonium chloride, trimethyldecylammonium chloride, tetramethylammonium bromide, tetra-n-butylammonium bromide, etc., or a phase transfer catalyst such as crown ether, etc.

By this reaction, it seems that a methyleneimine compound represented by the following formula (5):

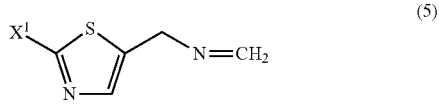

(5)

wherein $X^1$ is as defined above, which is an unstable intermediate would be formed once, followed by trimerization of the methyleneimine compound represented by the formula (5) to produce the hexahydrotriazine compound (2).

After completion of the reaction, the reaction mixture containing the hexahydrotriazine compound (2) is obtained, and the hexahydrotriazine compound (2) can be isolated, for example, by subjecting the reaction mixture to concentration treatment. Alternatively, by cooling the reaction mixture as it is or after subjected to partial concentration treatment, the hexahydrotriazine compound (2) can be isolated as crystals. Alternatively, the hexahydrotriazine compound (2) can be isolated by adding water and a hydrophobic organic solvent to the reaction mixture as it is or after subjected to concentration treatment to perform extraction, and concentrating the resulting organic layer. Alternatively, the hexahydrotriazine compound (2) can be isolated as an acid addition salt such as hydrochloride, sulfate, etc.

Examples of the hydrophobic organic solvent include halogenated hydrocarbon solvents such as chlorobenzene, dichlorobenzene, etc., ester solvents such as ethyl acetate, butyl acetate, etc., ketone solvents such as methyl ethyl ketone, methyl isobutyl ketone, etc., aromatic hydrocarbon solvents such as toluene, xylene, etc., and the like. These solvents can be used alone or in combination thereof. The amount of the solvent to be used is not specifically limited.

Alternatively, the reaction mixture or the organic layer containing the hexahydrotriazine compound (2) may be used in the subsequent step for producing the thiazole compound of the formula (3) described hereinafter without isolation of the hexahydrotrizine compound (2) from the reaction mixture.

Examples of thus-obtained hexahydrotriazine compound (2) include 1,3,5-tris{(thiazol-5-yl)methyl}-1,3,5-hexahydrotriazine, 1,3,5-tris{(2-chlorothiazol-5-yl)methyl}-1,3,5-hexahydrotriazine, 1,3,5-tris{(2-bromothiazol-5-yl)methyl}-1,3,5-hexahydrotriazine, etc.

Then, the step for reacting the resulting hexahydrotriazine compound (2) with hydroxylamine under acidic conditions to produce a thiazole compound represented by the formula (3):

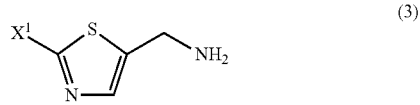

(3)

wherein $X^1$ is as defined above (hereinafter, abbreviated as thiazole compound (3)) will be explained.

This step is to react the hexahydrotriazine compound (2) with hydroxylamine under acidic conditions to produce the thiazole compound (3), and is usually performed by bringing into contact with and mixing the hexahydrotriazine compound (2) and hydroxylamine under acidic conditions.

As hydroxylamine, its free compound may be used, or an acid addition salt such as hydrochloride of hydroxylamine ($NH_2OH \cdot HCl$), and sulfate of hydroxylamine (($NH_2OH)_2 \cdot H_2SO_4$) may be used. As such hydroxylamine, commercially available hydroxylamine is usually used. In addition, such hydroxylamine may be used as it is, or may be used as a solution such as an aqueous solution.

The amount of such hydroxylamine to be used is usually 1 to 30 moles, preferably 1 to 15 moles, more preferably 1 to 10 moles per mole of the hexahydrotriazine compound (2).

The hexahydrotriazine compound (2) and hydroxylamine are brought into contact with and mixed under acidic conditions usually in an aqueous solution or in a mixed solvent of water and an organic solvent. The amount of water or a mixed solvent of water and an organic solvent to be used is usually 0.5 to 20 parts by weight per 1 part by weight of the hexahydrotriazine compound (2). When a mixture of water and an organic solvent is used, the ratio of mixing water and the organic solvent is not specifically limited. Examples of the organic solvent include aromatic hydrocarbon solvents such as toluene, xylene, etc., halogenated hydrocarbon solvents such as chlorobenzene, dichlorobenzene, etc., ether solvents such as diethyl ether, diisopropyl ether, methyl tert-butyl ether, tetrahydrofuran, etc., alcohol solvents such as methanol, ethanol, isopropanol, etc., and the like.

Examples of the acid to be used, when hydroxylamine is reacted under acidic conditions, include mineral acids such as hydrochloric acid, sulfuric acid, phosphoric acid, etc., and organic carboxylic acids such as acetic acid, propionic acid, citric acid, etc. A mineral acid is preferable, and hydrochloric acid or sulfuric acid is more preferable. The amount of the acid to be used is not specifically limited as far as hydroxylamine and the hexahydrotriazine compound (2) can be brought into contact with and mixed under acidic conditions.

Hydroxylamine may be added to the hexahydrotriazine compound (2), or the hexahydrotriazine compound (2) may be added to hydroxylamine. The temperature at which hydroxylamine is reacted is usually in the range of 0 to 100° C., preferably 0 to 50° C.

After hydroxylamine is reacted with the hexahydrotriazine compound (2) under acidic conditions and, if necessary, the reaction mixture is maintained for predetermined time, a solution of an acid addition salt of the thiazole compound (3) can be obtained, and then the acid addition salt of the thiazole compound (3) can be isolated by, for example, concentrating the solution.

When hydroxylamine is reacted with the hexahydrotriazine compound (2) under acidic conditions, formaldoxime as a reaction product of the reaction of hydroxylamine and formaldehyde or a trimer thereof is formed together with an acid addition salt of the thiazole compound (3). Therefore, it is preferable that, for example, the aforementioned solution containing an acid addition salt of the thiazole compound (3) is extracted by addition of a base and, if necessary, a hydrophobic organic solvent under basic conditions to separate into an organic layer containing the thiazole compound (3), and an aqueous layer containing formaldoxime or a trimer thereof. By concentration of the resulting organic layer, the thiazole compound (3) having a higher purity can be isolated. The isolated thiazole compound (3) may be converted into an acid addition salt such as hydrochloride, by reacting with an acid such as hydrochloric acid. Examples of the base include alkali metal hydroxide such as sodium hydroxide, etc., and the base is used usually at such an amount that the pH of the aqueous layer at the above extraction treatment is in the range of 8 to 14, preferably 10 to 14. Examples of the hydrophobic organic solvent include aromatic hydrocarbon solvents such as toluene, xylene, etc., halogenated hydrocarbon solvents such as chlorobenzene, dichlorobenzene, etc., ester solvents such as ethyl acetate and butyl acetate, and ketone solvents such as methyl ethyl ketone, methyl isobutyl ketone, etc., and the like.

These solvents can be used alone or in combination thereof. The amount of the solvent to be used is not specifically limited.

Further, an aqueous solution containing an acid addition salt of the thiazole compound (3) is obtained by mixing the organic layer containing the thiazole compound (3) obtained by the above extraction treatment, with an aqueous solution of an acid, followed by separating the mixture into layers. The acid addition salt of the thiazole compound (3) can be isolated by concentrating the aqueous solution containing an acid addition salt of the thiazole compound (3) as it is or by partially concentrating the aqueous solution. Alternatively, an insufficient solvent which hardly dissolves the acid addition salt of the thiazole compound (3) may be added to the aqueous solution containing the acid addition salt of the thiazole compound (3) to precipitate crystals of the acid addition salt of the thiazole compound (3). Examples of the aqueous solution of an acid include an aqueous solution of hydrochloric acid, sulfuric acid, acetic acid, methanesulfonic acid, etc. The aqueous solution is used at such an amount that the pH of the aqueous layer upon extraction is in a range of usually 2.5 to 5.5, preferably 3 to 5. Incidentally, when the resulting aqueous solution containing the acid addition salt of the thiazole compound (3) is colored, the aqueous solution may be subjected to decolorization, for example, by adding a decoloring agent such as active carbon to the aqueous solution.

Examples of thus-obtained thiazole compound (3) include 5-(aminomethyl)thiazole, 2-chloro-5-(aminomethyl)thiazole, 2-bromo-5-(aminomethyl)thiazole, etc.

EXAMPLES

The following Examples will further explain the present invention in more detail, but are not to be construed to limit the scope or the present invention. All the percents and parts are by weight, unless otherwise stated. For analysis, high performance liquid chromatography (LC) method was used.

Example 1

A stainless autoclave was charged with 3.69 parts (content: 92%) of paraformaldehyde, 21.8 parts of a 12.8% ammonia/methanol solution, 1.4 parts of methanol, and 6.96 parts (content: 97.6%) of 2-chloro-5-(chloromethyl)thiazole, and the mixture was reacted with stirring at an inner temperature of 40° C. for 3 hours, then at 50° C. for 3 hours, and further at 70° C. for 1 hour. The resulting reaction mixture containing 1,3,5-tris{(2-chlorothiazol-5-yl)methyl}-1,3,5-hexahydrotriazine was cooled to the inner temperature of 50° C., and concentrated under reduced pressure. To the resulting concentrated residue was added 24.4 parts of water, and the mixture was concentrated under reduced pressure. To the resulting concentrated residue was added 28.4 parts of toluene to perform extraction at the inner temperature of 70° C., thereby obtaining 36.5 parts of a toluene layer containing 1,3,5-tris{(2-chlorothiazol-5-yl)methyl}-1,3,5-hexahydrotriazine, and an aqueous layer. To the toluene layer was added 10.4 parts of water, and 13.9 parts of an aqueous solution of hydroxylamine sulfate (sulfate content: 23.8%) was added thereto over 2.5 hours. To the mixture was added 4.2 parts of 35% hydrochloric acid over 2 hours while maintaining the inner temperature at the range of 20 to 30° C. The mixture was retained at the same temperature for 30 minutes with stirring, and subjected to degradation treatment. To the mixture was added 20.9 parts of a 27% aqueous sodium hydroxide solution to adjust the pH to 13.6, and the resulting mixture was separated into layers to obtain an organic layer and an aqueous layer. The aqueous layer was extracted three times with toluene, and the resulting toluene layers were combined with the previously obtained organic layer. After washing the combined organic layer with 2.3 parts of a 14% aqueous sodium hydroxide solution, 9.1 parts of water was added thereto, and 3.6 parts of 35% by weight hydrochloric acid was further added thereto to adjust the pH to 4.6. Layers were separated, and 18.1 parts of the resulting aqueous layer was concentrated under reduced pressure condition to obtain 14.7 parts of the concentrated residue. To the concentrated residue was added water to obtain 15.7 parts (content: 41.8%) of an aqueous solution containing 2-chloro-5-(aminomethyl)thiazole hydrochloride. A yield of 2-chloro-5-(aminomethyl)thiazole hydrochloride was 87.6% (in terms of 2-chloro-5-(chloromethyl)thiazole), and a yield of bis{(2-chlorothiazol-5-yl)methyl}amine was 0.1% (in terms of 2-chloro-5-(chloromethyl)thiazole).

Reference Example 1

A glass autoclave was charged with 29.3 parts of 2-chloro-5-(chloromethyl)thiazole (content: 95.7%), 15.8 parts of paraformaldehyde (content: 95%) and 87.3 parts of a 13% ammonia/methanol solution, and the mixture was reacted by stirring at an inner temperature of 70° C. for 3 hours. A maximum value of an internal pressure (gauge pressure) during the reaction was 0.08 MPa. After completion of the reaction, the reaction mixture containing 2-chloro-5-(methylideneaminomethyl)thiazole was cooled to the inner temperature of 5° C., and the precipitated solid was collected by filtration. The collected solid was dried under reduced pressure to obtain 21.9 parts of 1,3,5-tris{(2-chlorothiazol-5-yl)methyl}-1,3,5-hexahydrotriazine.

MS (FD): m/z 480 at monoisotropic peak (C1×3 isotope pattern)

$^1$H-NMR (CDCl$_3$, 270 MHz, δ/ppm) 3.50 (brs, 2H), 3.82 (s, 2H), 7.33 (s, 1H)

$^{13}$C-NMR (CDCl$_3$, 68 MHz, δ/ppm) 48.85, 72.34, 138.73, 139.29, 151.71

Example 2

To a flask were added 5 parts of 1,3,5-tris{(2-chlorothiazol-5-yl)methyl}-1,3,5-hexahydrotriazine, 15 parts of toluene and 3.2 parts of 35% hydrochloric acid, and the mixture was retained at an inner temperature of 60° C. for 30 minutes with stirring. The mixture was cooled to the inner temperature of 35° C., and 18.3 parts of an aqueous solution of hydroxylamine sulfate (sulfate content: 14%) was added. To the mixture was added 13.2 parts of a 27% aqueous sodium hydroxide solution to adjust the pH to 12.2, and layers were separated to obtain the toluene layer containing 2-chloro-5-(aminomethyl)thiazole and an aqueous layer. The resulting aqueous layer was extracted two times with 15 parts of toluene, and the resulting toluene layers were combined with the previously obtained toluene layer containing 2-chloro-5-(aminomethyl)thiazole to obtain 49.4 parts (content: 8.5%) of a toluene solution containing 2-chloro-5-(aminomethyl)thiazole. A yield of 2-chloro-5-(aminomethyl)thiazole was 95.1% (in terms of 1,3,5-tris{(2-chlorothiazol-5-yl)methyl}-1,3,5-hexahydrotriazine).

Example 3

To a flask were added 28 parts of 1,3,5-tris{(2-chlorothiazol-5-yl)methyl}-1,3,5-hexahydrotriazine, 126 parts of toluene, 30.2 parts of water and 18.1 parts of 35% hydrochloric acid, and the mixture was retained at an inner temperature of 25° C. for 30 minutes with stirring. To the mixture was added 59.2 parts of an aqueous solution of hydroxylamine sulfate (sulfate content: 24%), and the mixture was retained at the inner temperature of 25° C. for 30 minutes with stirring. To the mixture was added 84 parts of a 27% aqueous sodium hydroxide solution to adjust the pH to 13 or higher, and layers were separated to obtain an organic layer containing 2-chloro-5-(aminomethyl)thiazole, and an aqueous layer. The resulting aqueous layer was extracted three times with toluene, and the resulting toluene layers were combined with the previously obtained organic layer containing 2-chloro-5-(aminomethyl)thiazole. After the combined organic layer was washed with 11.6 parts of a 14% aqueous sodium hydroxide solution, 41.9 parts of water was added thereto, and 17.9 parts of 35% hydrochloric acid was further added to adjust the pH to 4.6. Then, layers were separated to obtain an aqueous layer containing 2-chloro-5-(aminomethyl)thiazole hydrochloride. After the aqueous layer was concentrated, 0.3 part of active carbon was added to perform decolorization. After active carbon was filtered off, water was added to obtain 84.2 parts (content: 36.2%) of an aqueous solution containing 2-chloro-5-(aminomethyl)thiazole hydrochloride. A yield of 2-chloro-5-(aminomethyl)thiazole hydrochloride was 94.9% (in terms of 1,3,5-tris{(2-chlorothiazol-5-yl)methyl}-1,3,5-hexahydrotriazine).

Example 4

According to the same manner as that of Example 3 except that 17.1 parts of 50% sulfuric acid was used in place of 18.1 parts of 35% hydrochloric acid in Example 3, 85.3 parts (content: 35.7%) of an aqueous solution containing 2-chloro-5-(aminomethyl)thiazole hydrochloride was obtained. A yield of 2-chloro-5-(aminomethyl)thiazole hydrochloride was 94.4% (in terms of 1,3,5-tris{(2-chlorothiazol-5-yl)methyl}-1,3,5-hexahydrotriazine).

Example 5

To a flask were added 28 parts of 1,3,5-tris{(2-chlorothiazol-5-yl)methyl}-1,3,5-hexahydrotriazine, 126 parts of toluene, 30.2 parts of water, and 59.2 parts of an aqueous solution of hydroxylamine sulfate (sulfate content: 24%), and 18.1 parts of 35% hydrochloric acid was added dropwise thereto while an inner temperature of 20 to 30° C. was retained. Then, the mixture was retained at the inner temperature 25° C. for 30 minutes with stirring. Then, 85 parts of a 27% aqueous sodium hydroxide solution was added thereto to adjust the pH to 13 or higher, and layers were separated to obtain an organic layer containing 2-chloro-5-(aminomethyl)thiazole and an aqueous layer. The aqueous layer was extracted three times with toluene, and the resulting toluene layer was combined with the previously obtained organic layer. The combined organic layer was washed with 11.5 parts of a 14% aqueous sodium hydroxide solution. Then, 41.8 parts of water was added, and 17.8 parts of 35% hydrochloric acid was further added to adjust the pH to 4.7. Layers were separated, the resulting aqueous layer was concentrated, and 0.3 part of active carbon was added to perform decolorization. After active carbon was filtered off, water was added to obtain 84.8 parts (content: 36.9%) of an aqueous solution containing 2-chloro-5-(aminomethyl)thiazole hydrochloride. A yield of 2-chloro-5-(aminomethyl)thiazole hydrochloride was 96.8% (in terms of 1,3,5-tris{(2-chlorothiazol-5-yl)methyl}-1,3,5-hexahydrotriazine).

Example 6

According to the same manner as that of Example 5 except that 17.1 parts of 50% sulfuric acid was used in place of 18.1 parts of 35% hydrochloric acid in Example 5, 85.1 parts (content: 36.1%) of an aqueous solution containing 2-chloro-5-(aminomethyl)thiazole hydrochloride was obtained. A yield of 2-chloro-5-(aminomethyl)thiazole hydrochloride was 95.2% (in terms of 1,3,5-tris{(2-chlorothiazol-5-yl)methyl}-1,3,5-hexahydrotriazine).

Example 7

To a flask were added 5 parts of 1,3,5-tris{(2-chlorothiazol-5-yl)methyl}-1,3,5-hexahydrotriazine, 15 parts of toluene, 15 parts of water and 3.3 parts of 35% hydrochloric acid, and the mixture was retained at an inner temperature of 60° C. for 30 minutes with stirring. After the mixture was cooled to the inner temperature of 25° C., 2.3 parts (content: 97%) of hydroxylamine hydrochloride was added. To the mixture was added 11.6 parts of a 27% aqueous sodium hydroxide solution was added to adjust the pH to 12.3, and layers were separated to obtain 18.3 parts (content: 17.5%) of a toluene solution containing 2-chloro-5-(aminomethyl)thiazole. A yield of 2-chloro-5-(aminomethyl)thiazole was 72% (in terms of 1,3,5-tris{(2-chlorothiazol-5-yl)methyl}-1,3,5-hexahydrotriazine).

Example 8

To a flask were added 5 parts of 1,3,5-tris{(2-chlorothiazol-5-yl)methyl}-1,3,5-hexahydrotriazine, 15 parts of toluene, and 3.3 parts of 35% hydrochloric acid, and the mixture was retained at an inner temperature of 60° C. for 30 minutes with stirring. After the mixture was cooled to the inner temperature of 25° C., 10.6 parts of an aqueous solution of hydroxylamine sulfate (sulfate content: 24%) was added. To the mixture was added 12.4 parts of a 27% aqueous sodium hydroxide solution to adjust the pH to 12.3, and layers were separated to obtain 18.9 parts (content: 18.5%) of a toluene solution containing 2-chloro-5-(aminomethyl)thiazole. A yield of 2-chloro-5-(aminomethyl)thiazole was 75.8% (in terms of 1,3,5-tris{(2-chlorothiazol-5-yl)methyl}-1,3,5-hexahydrotriazine).

Example 9

According to the same manner as that of Example 8 except that 9 parts of an aqueous solution of hydroxylamine hydrochloride (hydrochloride content: 24%) was used in place of 10.6 parts of an aqueous solution of hydroxylamine sulfate (sulfate content: 24%) in Example 8, 18.6 parts (content: 17.5%) of a toluene solution containing 2-chloro-5-(aminomethyl)thiazole was obtained. A yield of 2-chloro-5-(aminomethyl)thiazole was 70.2% (in terms of 1,3,5-tris{(2-chlorothiazol-5-yl)methyl}-1,3,5-hexahydrotriazine).

Example 10

To a flask were added 5 parts of 1,3,5-tris{(2-chlorothiazol-5-yl)methyl}-1,3,5-hexahydrotriazine, 15 parts of toluene, and 3.2 parts of 35% hydrochloric acid, and the mixture was retained at an inner temperature of 60° C. for 30 minutes with stirring. After the mixture was cooled to the inner temperature of 35° C., 18.3 parts of an aqueous solution containing hydroxylamine sulfate (sulfate content: 14%) was added. To the mixture was added 13.2 parts of a 27% aqueous sodium hydroxide solution to adjust the pH to 12.2, and layers were separated to obtain 18.3 parts (content: 17.3%) of a toluene solution containing 2-chloro-5-(aminomethyl)thiazole. A yield of 2-chloro-5-(aminomethyl)thiazole was 71.6% (in terms of 1,3,5-tris{(2-chlorothiazol-5-yl)methyl}-1,3,5-hexahydrotriazine).

Comparative Example 1

A stainless autoclave was charged with 15.7 parts of 2-chloro-5-(chloromethyl)thiazole (content: 95.7%) and 25.4 parts of a 24% ammonia/methanol solution, and the mixture was reacted by stirring at an inner temperature of 70° C. for 3 hours. A maximum value of an internal pressure (gauge pressure) during the reaction was 0.28 MPa. After the resulting reaction mixture was transferred to another flask while washing in with about 15 parts of methanol, the mixture was concentrated under reduced pressure to obtain 26.1 parts of the concentrated residue. To the concentrated residue was added methanol to obtain 228 parts of a solution containing 2-chloro-5-(aminomethyl)thiazole. A yield of 2-chloro-5-(aminomethyl)thiazole was 41.4% (in terms of 2-chloro-5-(chloromethyl)thiazole, and a yield of bis{(2-chlorothiazol-5-yl)methyl}amine was 24.5% (in terms of 2-chloro-5-(chloromethyl)thiazole).

INDUSTRIAL APPLICABILITY

According to the present invention, a thiazole compound which is useful as an intermediate for medicine and agrochemicals can be industrially advantageously produced while production of a byproduct is suppressed.

The invention claimed is:

1. A process for producing a thiazole compound represented by the formula (3):

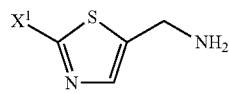
(3)

wherein $X^1$ represents a hydrogen atom or a halogen atom, which comprises the steps of reacting a compound represented by the formula (1):

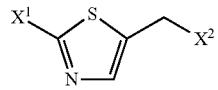
(1)

wherein $X^1$ is as defined above, and $X^2$ represents a halogen atom, with ammonia and formaldehyde to obtain a hexahydrotriazine compound represented by the formula (2):

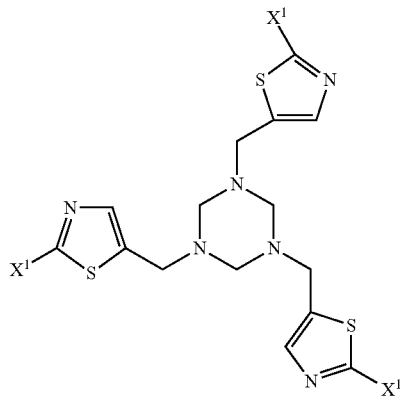
(2)

wherein $X^1$ is as defined above, and, then, reacting the resulting hexahydrotriazine compound represented by the formula (2) with hydroxylamine under acidic conditions.

2. The process according to claim 1, wherein the amount of hydroxylamine to be used is 1 to 10 moles per mole of the hexahydrotriazine compound represented by the formula (2).

3. The process according to claim 1, wherein formaldehyde is in the form of paraformaldehyde or formalin.

4. The process according to claim 1, wherein the amount of formaldehyde to be used is 1 to 10 moles per mole of the compound represented by the formula (1).

5. The process according to claim 1, wherein the amount of ammonia to be used is 2 to 10 moles per mole of the compound represented by the formula (1).

6. The process according to claim 1, wherein, after the reaction of the hexahydrotriazine compound represented by the formula (2) with hydroxylamine, the reaction mixture is extracted with a hydrophobic organic solvent under basic conditions to separate an organic layer containing the thiazole compound represented by the formula (3).

7. A process for producing a thiazole compound represented by the formula (3):

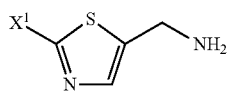
(3)

wherein $X^1$ represents a hydrogen atom or a halogen atom, which comprises reacting a hexahydrotriazine compound represented by the formula (2):

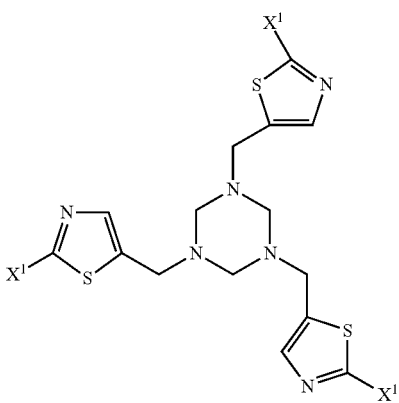
(2)

wherein $X^1$ is as defined above, with hydroxylamine under acidic conditions.

8. The process according to claim 7, wherein, after the reaction of the hexahydrotriazine compound represented by the formula (2) with hydroxylamine, the reaction mixture is extracted with a hydrophobic organic solvent under basic conditions to separate an organic layer containing the thiazole compound represented by the formula (3).

* * * * *

UNITED STATES PATENT AND TRADEMARK OFFICE
CERTIFICATE OF CORRECTION

PATENT NO. : 7,977,490 B2
APPLICATION NO. : 11/918004
DATED : July 12, 2011
INVENTOR(S) : Kazuyuki Tanaka et al.

It is certified that error appears in the above-identified patent and that said Letters Patent is hereby corrected as shown below:

ON THE TITLE PAGE:
Item (86) should be changed as follows:

"PCT No.:    PCT/JP2006/307682
&371 (c)(1),
(2),(4) Date:   November 19, 2008"

to

--PCT No.:    PCT/JP2006/307682
&371 (c)(1),
(2),(4) Date:   November 19, 2007--.

Signed and Sealed this
Thirteenth Day of September, 2011

David J. Kappos
*Director of the United States Patent and Trademark Office*